(12) United States Patent
Duffy et al.

(10) Patent No.: US 6,203,996 B1
(45) Date of Patent: Mar. 20, 2001

(54) RAPID DETECTION OF BACTERIA LIQUID CULTURES

(75) Inventors: Geraldine Duffy; James Sheridan, both of Dublin (IE)

(73) Assignee: Teagasc, The Agriculture and Food Development Authority, Dublin (IE)

(*) Notice: Subject to any disclaimer, the term of this patent is extended or adjusted under 35 U.S.C. 154(b) by 0 days.

(21) Appl. No.: 08/702,651

(22) PCT Filed: Feb. 28, 1995

(86) PCT No.: PCT/IE95/00021

§ 371 Date: Oct. 21, 1996

§ 102(e) Date: Oct. 21, 1996

(87) PCT Pub. No.: WO95/23872

PCT Pub. Date: Sep. 8, 1995

(30) Foreign Application Priority Data

Mar. 1, 1994 (IE) .................................................. S940182

(51) Int. Cl.[7] ........................ G01N 33/53; G01N 33/554; G01N 1/30; C12N 1/00

(52) U.S. Cl. .............................. 435/7.2; 435/7.35; 435/8; 435/7.94; 435/7.32; 435/7.9; 435/975; 435/870; 435/7.95; 435/40.51; 530/387.1; 530/388.4; 530/389.5

(58) Field of Search .................... 435/7.2, 8, 7.35, 435/7.94, 7.32, 7.9, 7.95, 975, 870, 40.51; 530/387.1, 388.4, 389.5

(56) References Cited

U.S. PATENT DOCUMENTS

| | | |
|---|---|---|
| 3,989,591 | 11/1976 | Liotta . |
| 4,552,839 * | 11/1985 | Gould et al. . |
| 4,870,158 * | 9/1989 | Karol et al. . |
| 5,085,982 * | 2/1992 | Keith . |
| 5,135,851 * | 8/1992 | Kajander . |
| 5,139,933 * | 8/1992 | Green et al. . |
| 5,212,062 * | 5/1993 | Daniels et al. . |
| 5,221,612 * | 6/1993 | Zhau et al. . |
| 5,293,210 * | 3/1994 | Berndt . |
| 5,354,654 * | 10/1994 | Ligler et al. . |
| 5,403,718 * | 4/1995 | Dorward et al. . |
| 5,462,860 * | 10/1995 | Mach . |
| 5,510,242 * | 4/1996 | Blais et al. . |
| 5,529,904 * | 6/1996 | Ginsburg et al. . |
| 5,627,275 * | 5/1997 | Roll . |

FOREIGN PATENT DOCUMENTS

| | | |
|---|---|---|
| 0281477 | 3/1988 | (EP) . |
| 0429794 | 9/1990 | (EP) . |
| 0498920 | 5/1991 | (EP) . |
| 0511110 | 4/1992 | (EP) . |
| 61-092597 * | 5/1986 | (JP) . |
| 02065798 * | 3/1990 | (JP) . |

OTHER PUBLICATIONS

McLaughlin etal Letters in Applied Microbiology 8/1:25–27, 1988.*
Herald etal, J. Food Science 53/8:1549–1562, 1988.*
Mafu etal, J. Food Protection 53/9:742–746, 1998.*
Scacchi etal, Pestic Sci. 45:49–56, 1995.*
Sheridan etal, J.Applied Microbiol. 82:225–32, 1997.*
Todd etal, Food Microbiol, 8:311–324, 1991.*
Absolom, D.R. et al., "Surface Thermodynamics of Bacterial Adhesion," *Applied and Environmental Microbiology* (1983) 46(1):90–97.
Brown, M.R.W. et al., "The influence of environment on envelope properties affecting survival of bacteria in infections," *Annual Review of Microbiology* (1985) 39:527–556.
Chung, K.–T. et al., "Attachment and Proliferation of Bacteria on Meat," *Journal of Food Protection* (1989) 52(3):173–177.
Dazzo, F.B. "Microbial adhesion to plant surfaces," Chapter 17, Michigan Agricultural Experiment Station Journal Series No. 9231 (1980) 311–324.
Dickson, J.S. et al., "Attachment of *S. typhimurium* and *L. monocytogenes* to glass as affected by surface film thickness, cell density and bacterial motility," *Journal Industrial Microbiology* (1991) 8:281–284.
Donnelly, C.W. et al., "Method for flow cytometric detection of *Listeria monocytogenes* in milk," *Applied Environmental Microbiology* (1986) 52(4):689–695.
Duffy, G. et al., "The use of Alcalase 2.5L in the Acridine orange direct count technique for the enumeration of bacteria in beef mince," *Letters in Applied Microbiology* (1991) 13:198–201.
Duffy, G. et al., "The effect of aeration, initial inoculum and meat microflora on the growth kinetics of *L. monocytogenes* in selective broths," *Food Microbiology* (1994) 11:429–438.
Farber, J.M. et al., "Attachment of psychrotrophic meat spoilage bacteria to muscle surfaces," *Journal of Food Protection* (1984) 47(2):92–95.
Firstenberg–Eden, R. et al., "Attachment of certain bacterial strains to chicken and beef meat," *Journal of Food Safety* (1978) 1:217–228.
Firstenberg–Eden, R., "Attachment of bacteria to meat surfaces: A review," *Journal of Food Protection* (1981) 8:602–607.
Fletcher, M., "The effects of culture concentration and age, time, and temperature on bacterial attachment to polystyrene," *Canadian Journal of Microbiology* (1977) 23:1–6.

(List continued on next page.)

Primary Examiner—Nita Minnifield
(74) Attorney, Agent, or Firm—Morrison & Foerster LLP

(57) ABSTRACT

A means for the rapid detection of bacteria from a liquid culture or slurry is described. A membrane mounted on a solid support is immersed in a liquid culture for a time sufficient to allow bacteria to adhere to the membrane, the membrane is removed from the culture and the number of bacteria adhering to the membrane is counted. The membrane may be either an inanimate membrane or a biological membrane. A test kit for use in the method is also described.

25 Claims, 2 Drawing Sheets

OTHER PUBLICATIONS

Figure 1:
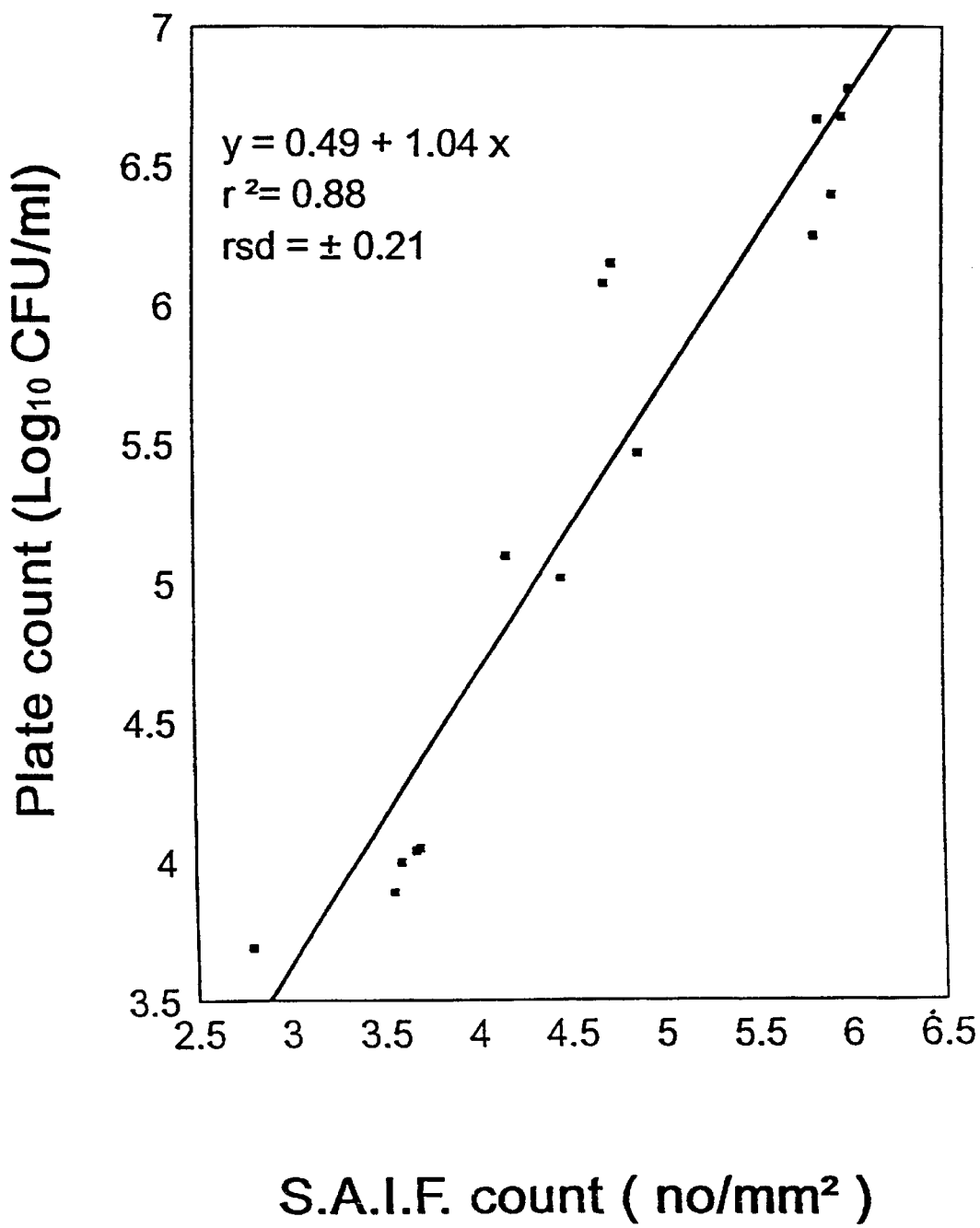

Fletcher, M. et al., "An electron–microscopic demonstration of an acidic polysaccharide involved in the adhesion of marine bacterium to solid surfaces," *Journal of General Microbiology* (1973) 74:325–334.

Fletcher, M. et al., "Influence of substratum characteristics on the attachment of a marine pseudomonad to solid surfaces," *Applied Environmental Microbiology* (1979) 37(1):67–72.

Gelinas, P. et al., "Efficacite de huit desinfectants sur trois types de surfaces contaminees par *Ps. aeruginosa*," *Canadian Journal of Microbiology* (1983) 24:1715–1730.

Herald, P.J. et al., "Attachment of *L. monocytogenes* to stainless steel surfaces at various temperatures and pH values," *Journal of Food Science* (1988) 53(5):1549–1552.

Kim, J.–W. et al., "Penetration of *Salmonella typhimurium* into turkey skin," *Journal of Food Protection* (1993) 56:292–296.

Kroll, R.G., "Electropositively charged filters for the concentration of bacteria from foods," *Food Microbiology* (1980) 2:183–186.

Litopoulou–Tzanetaki, E. et al., "Adsorption of bacteria to ion–exchange materials," *Letters in Applied Microbiology* (1989) 9:219–222.

Mafu, A.A., "Attachment of *L. monocytogenes* to stainless steel, glass, polypropylene and rubber surfaces after short contact times," *Journal of Food Protection* (1990) 53(9):742–746.

McClain, D. et al., "Isolation and identification of *L. monocytogenes* from meat," USDA–FSIS Microbiol. Div., Laboratory Communication No. 57 (1987).

Rossen, L. et al., "A rapid polymerase chain reaction (PCR) based assay for the identification of *Listeria monocytogenes* in food samples," *International Journal of Food Microbiology* (1991) 14:145–151.

Selgas, D. et al., "Attachment of bacteria to meat surfaces: A review," *Meat Science* (1993) 34:265–273.

Sheridan, J.J. et al., "Use of a microcolony technique combined with an indirect immunofluorescence test for the rapid detection of Listeria in raw meat," *Letters in Applied Microbiology* (1991) 13:140–144.

Sheridan, J.J. et al., "The occurrence and initial numbers of Listeria in Irish meat and fish products and the recovery of injured cells from frozen products," *International Journal of Food Microbiology* (1994) 22:105–113.

Sheridan, J.J. et al., "Development of a surface adhesion immunofluorescent technique for the rapid isolation of *Listeria monocytogenes* and *Listeria innocua* from meat," *J App Microbiol* (1997) 82:1–8.

Thomas, D.S. "Electropositively charged filters for the recovery of yeasts and bacteria from beverages," *Journal of Applied Bacteriology* (1988) 65:35–41.

van Loosdrecht, M.C.M. et al., "The role of bacterial cell wall hydrophobicity in adhesion," *Applied Environmental Microbiology* (1987) 53:1893–1897.

Walker, P.D. et al., Adhesion of organisms to animal tissues, Chapter 26, Ellis Horwood Ltd. Publishers (1980) 473–493.

Walker, S.J. et al., "Comparison of the Listeria–tek ELISA kit with cultural procedures for the detection of Listeria sps. in foods," *Food Microbiology* (1990) 7:335–342.

Walls, I. et al., "A rapid method of enumerating microorganisms from beef, using an Acridine Orange Direct Count technique," *Irish Journal of Food Science Technology* (1989) 13:23–31.

Walls, I. et al., "Factors affecting attachment of *Salmonella typhimurium* to sausage casings," *Food Microbiology* (1993) 10:387–393.

Wood, J.M. "The interaction of microorganisms with ion–exchange resins," Chapter 8 in: *Microbiol Adhesion to Surfaces*, ed. Berkeley, R.C.W., et al., pp. 163–185. Chichester: Ellis Horwood.

* cited by examiner

RAPID DETECTION OF BACTERIA LIQUID CULTURES

The present invention relates to a means of rapid detection of bacteria from a liquid culture or slurry. The liquid culture may be a true liquid such as milk but it may also be produced by suspending a solid in a liquid or mincing or macerating the solid therein.

The attachment of bacteria to solid surfaces is a well known phenomenon. The ease with which microorganisms accumulate at surfaces is the cause of numerous economic and biological problems. Microorganisms will readily colonize man-made structures immersed in aqueous environments which can lead to corrosion and fouling (Herald and Zottola, 1988). Many diseases of animal and plants result from the growth of pathogenic microorganisms on host epithelial surfaces (Walker and Nagy, 1980; Dazzo, 1980).

The attachment of bacteria to food surfaces including meat contributes to food spoilage and the risk of food poisoning (Selgas et al., 1993, Firstenberg-Eden, 1981), for example, *Listeria monocytogenes* is an important food borne pathogen which may contaminate meat, cheese and other foodstuffs. A number of authors have reported the attachment of *L. monocytogenes* to solid surfaces including glass, stainless steel, polypropylene and rubber surfaces (Dickson and Daniels, 1991, Mafu et al. 1990, Fletcher and Loeb, 1979).

Jeong-Weon et al. (1993) described the adhesion of *Salmonella typhimurium,* another important food pathogen, to turkey skin. These authors showed that the attachment of the pathogen was much higher to skin surfaces on which the collagen fibers were exposed. This suggests that there is a specific receptor in the collagen fiber which binds to Salmonella. This view was corroborated by Walls et al., (1993) who used sausage casing as a model for the attachment of Salmonella to meat. The attachment of Salmonella to collagen fibers can be used as a model for the attachment of a number of important pathogens to meat.

Bacterial attachment to solid surfaces is believed to be influenced by cell surface charge (Fletcher & Loeb, 1979), hydrophobicity (van Loosdrecht et al., 1987) and by the presence of particular surface structures such as flagella, fimbriae, and extracellular polysaccharides (Fletcher & Floodgate, 1973). Abolosom et al., (1983) reported that attachment was greatest for hydrophobic organisms. Of five organisms examined by these authors, *L. monocytogenes* was the most hydrophobic and showed the greatest amount of attachment.

It is possible that an increased concentration of a particular bacterial species in a liquid medium leads to an increase in the number of collisions with the surface (Fletcher, 1979). Chung et al. (1989) reported that in the simultaneous presence of *L. monocytogenes* and *Pseudomonas aeruginosa* no significant competitive attachment between the two species occurred. This is relevant because previous studies have shown that the pseudomonads form part of the meat microflora growing during incubation of both selective and non selective enrichment broths (Duffy et al., 1994). Farber and Idziak (1984) also reported that, in general, the attachment of one organism to meat was unaffected by the presence of another organism.

Many rapid methods for the detection of bacteria employ specialised kit systems which are very expensive (Listeria-tek, Gene-trak). Techniques such as Gene-trak are labour intensive while flow cell cytometry techniques require operators to have specialised training (Donnelly and Baigent, 1986). The electrical based methods such as conductance and impedance are currently the simplest to carry out and have been automated.

EP-A-0 429 794 A2 discloses an assay method for detecting Listeria which is an immunoassay characterised by the combined use of antibodies specific for two separate cell wall components, namely peptidoglycan and teichoic acids, the antibodies being immobilised on a solid support.

EP-A-0 498 920 A2 also relates to an assay method for detecting the presence of bacteria or other culturable organisms. It involves an immunoassay method to detect the presence of viable bacteria strains in foods and other potentially contaminated samples using an assay characterised by
  (1) capture of specific bacteria cells with specific antibodies immobilised on a solid support;
  (2) incubation of the captured cells to form bacteria colonies;
  (3) imprint of the colonies to a colony lift membrane; and
  (4) immunochemical detection and species identification of the colonies on the colony lift membrane.

EP-A-0 281 477 A1 describes a method in which spores are detected by coupling the spores with a labelled monoclonal anti-spore antibody, depositing the resultant antigen—antibody complex on a gel containing a substrate for the label and a detector syste to show deposited complex. U.S. Pat. No. 3,989,591 describes a method of isolating and/or separating bacteria and tissue cells for testing or rapid automatic screening using an expandable membrane on which the tissue cell or bacteria sample is placed and subsequently expanded to cause the sample to be separated. EP-A-0 511 110 A2 describes a method of separating bacteria comprising passing bacteria-containing fluid through a ceramic membrane on a ceramic support in order to sterilise the liquid by filtration.

It is an object of the present invention to provide a method for the isolation and detection of bacteria from a liquid culture, which is simple to perform, rapid, inexpensive, non-labour intensive and sensitive. In particular, the invention seeks to provide a method for the detection of microbial pathogens in foodstuffs. The invention also seeks to provide a method of detection of microorganisms for use as a clinical or medical diagnostic test.

The present invention provides a method of rapid detection of bacteria in a liquid culture suspected to contain bacteria wherein a membrane mounted on a support is immersed in a liquid culture for a time sufficient to allow bacteria to adhere to the membrane, the membrane is removed from the liquid culture and the number of bacteria adhering to the membrane is counted.

The membrane may be an inanimate membrane such as a polycarbonate membrane; a membrane based on a cellulose derivative such as an acetate, nitrate or ester derivative; a polyvinyl chloride membrane; a polyamide membrane; a nylon membrane or an inorganic membrane such as a silver or aluminium membrane. An ion exchange membrane may be used to give a selective separation of the organisms.

Alternatively the membrane may be a biological membrane such as animal skin, animal intestinal membrane or other animal internal membrane, or a sausage casing membrane or a collagen membrane. Biological membranes may be advantageous for more selective isolation of microorganisms.

The solid support on which the membrane is mounted may be a glass microscope slide, plastics slide, wire or other suitable frame. The solid support should be sterilisable. Any support to which a membrane can be temporarily be attached is suitable for use.

The membrane may be immersed in the liquid culture for a least 10 minutes, and preferably at least 15 minutes, at between 25 and 30° C.

Preferably the method also comprises the step of coating the membrane with a labelled anti-bacterial antibody following removal of the membrane from the liquid culture. The antibody is most suitably a monoclonal antibody.

The anti-bacterial antibody may be an anti-Listeria antibody, or an anti-Yersinia antibody.

The membrane may be washed between removal from the liquid culture and coating with the antibody.

The label may be selected from fluorescein isothiocyanate, tetramethylrhodamine, horseradish peroxidase, alkaline phosphatase, glucose oxidase or any other label known in the art.

If a fluorescent label is employed, the membrane may be examined under an ultra-violet light microscope and a count of fluorescing labelled bacterial cells made, preferably, in a plurality of fields. Alternatively a laser system may be used to scan the membrane and count labelled cells.

The liquid culture may be prepared by immersion of a solid or semi-solid substance in a liquid such as an enrichment broth. The solid or semi-solid substance may be minced or macerated before immersion in the liquid.

The invention also provides a test kit for the rapid detection of bacteria in a liquid culture suspected to contain bacteria comprising a membrane mounted on a solid support and a labelled anti-bacterial antibody. The kit may additionally comprise an enzyme-labelled conjugate or a fluorescent-labelled conjugate. The kit may also comprise a substrate such as O-phenylenediamine dihydrochloride or tetramethylbenzidine.

The membrane may be an inanimate membrane such as a polycarbonate membrane, a polyvinyl chloride membrane, or a membrane based on a cellulose derivative such as an acetate, nitrate or an ester derivative or a biological membrane such as animal skin, an animal intestinal membrane or other animal internal membrane.

The invention also provides a membrane mounted on a solid support for use in the detection of bacteria in a liquid culture.

The invention will now be described in greater detail with reference to the following Examples.

EXAMPLE 1

MEAT SAMPLES

Minced beef samples were obtained from the abattoir of the industrial development unit on site or from local retail outlets. Meat samples used in inoculation experiments were screened for the presence of naturally occurring Listeria using the USDA recommended procedure (McClain & Lee, 1988).

ANTI-LISTERIA MONOCLONAL ANTIBODY

Mouse anti *L. monocytogenes* monoclonal antibody was diluted 1/50 (v/v) in a 1% solution of skim milk powder (Marvel, U.K.) with 0.1% Tween 80 then dispensed into 5.0 ml volumes and stored at −18° C., for up to 12 months. This antibody reacts with all *L. monocytogenes* serovar 4b, some strains of *L. monocytogenes* serogroup 4 and some strains of *L. innocua*.

FLUORESCEIN ISOTHIOCYANATE

Fluorescein isothiocyanate (FITC)—labelled anti-mouse antibody (Tissue Culture Services, Botolph, Claydon, Buckingham, UK) was diluted 1/50 (v/v) in a 1% solution of skim milk powder (Marvel) containing 0.1% Tween 80. The solution was stored at −18° C. for up to 12 months.

*L. MONOCYTOGNES* INOCULUM

*L. monocytogenes* was streaked onto Tryptone Soya Agar (TSA) (Oxoid, Bassingstoke, Hants., U.K.) and incubated overnight at 30° C. An isolated colony was picked off the TSA plate using a sterile loop and dispersed into 9.0 ml of 0.1% peptone water (Difco, Detroit, Mich., USA). The number of *L. monocytogenes* per ml of suspension was determined using a membrane filtration epifluorescent technique (Walls et al. 1989). Briefly, a 1.0 ml aliquot was pipetted from the suspension and filtered through a 0.6 μm polycarbonate membrane (Nucleopore, Calif., USA). The bacteria on the membrane were stained with acridine orange and counted under UV light using a fluorescent microscope (Nikon) with an epifluorescent attachment and a 100 W mercury vapour lamp as a light source. The organisms were counted as described by Walls et al. (1989). The original *L. monocytogenes* suspension was serially diluted to give the desired inoculum level in the suspension.

MEAT CULTURE SYSTEM

Minced beef was inoculated with *L. monocytogenes* (10.0 CFU/g) and placed in 225 ml of enrichment broth BPW (Buffered Peptone Water (BBL, Becton Dickson, Cockeysville, Md., USA). The meat culture was poured into a sterile glass trough (Lennox laboratory supplies, Dublin) designed for histological staining techniques. The trough had a flat lid and was grooved internally to hold 20 slides. The culture was incubated overnight (18 h) at 30° C.

ISOLATION OF CELLS BY SURFACE ADHESION

A polycarbonate membrane (0.6 μm, Poretics, Calif., USA) was placed on the surface of a sterile microscope glass slide (35 mm×70 mm). A clean metal ring (outer diameter 25 mm. inner diameter 18 mm) was placed on top of the membrane and secured with elastic bands. The purpose of the metal ring was to ensure that a defined area (10.17 mm$^2$) on one surface of the membrane was exposed to the culture. The slide was placed in the staining trough containing the meat culture to allow bacteria to adhere to the exposed membrane surface.

RELATIONSHIP BETWEEN IMMERSION TIME AND NUMBER OF BACTERIA ADHERING TO A MEMBRANE

Inoculated meat cultures were prepared and incubated overnight at 30° C. Polycarbonate membranes (n=8) were attached to sterile glass slides and immersed in the staining trough containing the test culture for 5, 10, 15, 20, 30, 40, 50 and 60 minutes respectively. Following immersion, the membranes were detached from the slides and the numbers of organisms on the membrane surface were determined using standard plating techniques. The procedure used was based on the rinse method described by Firstenberg-Eden et al. (1978) to count the number of bacteria on meat surfaces. The membrane was placed in peptone water (0.1%) (10.0 ml) and shaken vigorously for 1 minute to detach the cells from the membrane into the suspension. Aliquots of 0.1 ml were plated onto Listeria selective agar (Palcam, Lab M) and Plate count agar (PCA) and the number of Listeria and the TVC in the 10.0 ml suspension were calculated.

To determine if all cells were removed from the membrane, it was removed from the 0.1% peptone water suspension and placed on the surface of a selective agar plate. The plate was incubated at 30° for 48 h and the membrane was then examined for the development of Listeria colonies.

The number of Listeria in the peptone water suspension plus the number of cells detected on the membrane corresponded to the number of Listeria cells which were on the membrane surface. The experiment was preformed in duplicate and repeated on three occasions.

To investigate the effect of antibiotics on bacterial attachment, the above experiment was carried out in both a selective broth (UVM 1, Oxoid) and a nonselective broth (BPW). t-tests were used to compare the number of bacteria attached to membranes immersed in UVM I broth and BPW.

DETECTION OF LISTERIA BY IMMUNOFLUORESCENCE MICROSCOPY

Listeria cells were isolated from the test culture using the surface adhesion technique described above. Following immersion in the trough containing the culture for 15 min, the membrane was washed to remove debris. The membrane was placed on a filter tower and phosphate buffered saline (PBS) (20.0 ml) was filtered through the membrane with the aid of a vacuum pump. The membrane was coated with anti-Listeria monoclonal antibody and fluorescein isothiocyanate as described by Sheridan et al (1991).

A Nikon Optiphot microscope with an epifluorescent attachment, a 100 Watt mercury vapour light source and a 60× oil immersion plan objective was used to examine the membrane for the presence of bright green fluorescing Listeria cells which were clearly distinguishable from other bacteria on the membrane. The total number of Listeria cells were counted in 20 different fields of vision. The number of cells counted were multiplied by a working factor to obtain the number of Listeria per mm$^2$, the factor being 318.

DETERMINATION OF LISTERIA NUMBERS BY A STANDARD PLATE COUNT AND A SURFACE ADHESION-IMMUNOFLUORESCENT TECHNIQUE

Meat culture systems (n=15) were prepared and plate counts (Listeria and TVC) were carried out after 8, 10, 12, 14, 16, 18 and 20 h incubation. At each sampling time, duplicate membranes were placed in the meat culture systems for 15 min. On one of these membranes the number of bacteria attached was determined using the rinse method described above. While the other membrane was examined using immunofluorescence microscopy.

Regression analysis was used to investigate the relationship between time and (a) the number of Listeria and meat microflora in the culture and (b) the number of Listeria and meat microflora isolated onto the membrane by surface adhesion. The relationship between Listeria standard plate counts and the immunofluorescent counts was also determined using regression analysis. The data from this study was used to determine the detection level of the surface adhesion immunofluorescent (S.A.I.F.) method.

VALIDATION OF SURFACE ADHESION IMMUNOFLUORESCENT TECHNIQUE

The S.A.I.F. technique was used to detect naturally occurring Listeria from commercial beef mince samples (n=50). Commercial minced beef samples (25.09) were placed in 225 ml BPW and incubated at 30° C. Following 14 h incubation, Listeria was isolated from the culture by surface adhesion onto a membrane and detected by immunofluorescence. If the sample was negative after 14 hours incubation, the test was repeated after 18 hours incubation. Incubation was continued for 48 h and sample was examined for the presence of Listeria using standard techniques. The species present was also identified (Sheridan et al., 1994).

The regression equation generated to predict the Listeria plate count from the S.A.I.F. count was validated using the data from the commercial samples. The S.A.I.F. counts from the commercial samples were used to predict the Listeria plate counts from the original regression equation. The relationship between the S.A.I.F. counts and the predicted standard plate counts was determined by linear regression analysis.

The data in Table 1 shows the number of Listeria cells and microorganisms adhering to a membrane when immersed for different periods of time in a meat culture. The results show that the optimum attachment of Listeria to the membrane occurred after 15 minutes immersion. Attachment of the meat microorganisms was also at an optimum after immersion for 15 min.

There was no significant difference in the adhesion of Listeria or meat microorganisms to membranes immersed at the same time in either selective or nonselective broths.

Table 2 shows the numbers of Listeria and meat microorganisms/ml of culture at successive sampling times and the number of Listeria and meat microorganisms isolated onto the membrane by the surface adhesion technique. While the number of Listeria in the culture increased linearly with time (R=0.98), the number of meat microorganisms (TVC) in the culture reached a maximum population density after 14 h incubation. Similarly, the number of Listeria attaching to the membrane increased linearly with time (R=0.98) while the number of meat microorganisms adhering to the membrane remained static after 14 h incubation.

When the number of Listeria cells in the culture reached a level of $\geq \text{Log}_{10} 3.01$ they were detectable by the S.A.I.F (Table 2).

The relationship between the number of Listeria in the culture and the number of Listeria detected by the S.A.I.F. method was shown to be linear ($R^2$=0.88) (FIG. 1). The regression equation generated can be used to predict the number of Listeria /ml culture from immunofluorescent counts (RSD=+0.21).

The results obtained when commercial samples were examined for the presence of Listeria by the standard method of detection and a surface-adhesion immunofluorescent technique are shown in Table 3. Using the S.A.I.F. method no false positive results were reported. Two false negatives occurred. Using standard identification techniques the samples were shown to contain *Listeria welshimeri* species only. The antibody used in this assay does not react with these Listeria species.

Figure 2:
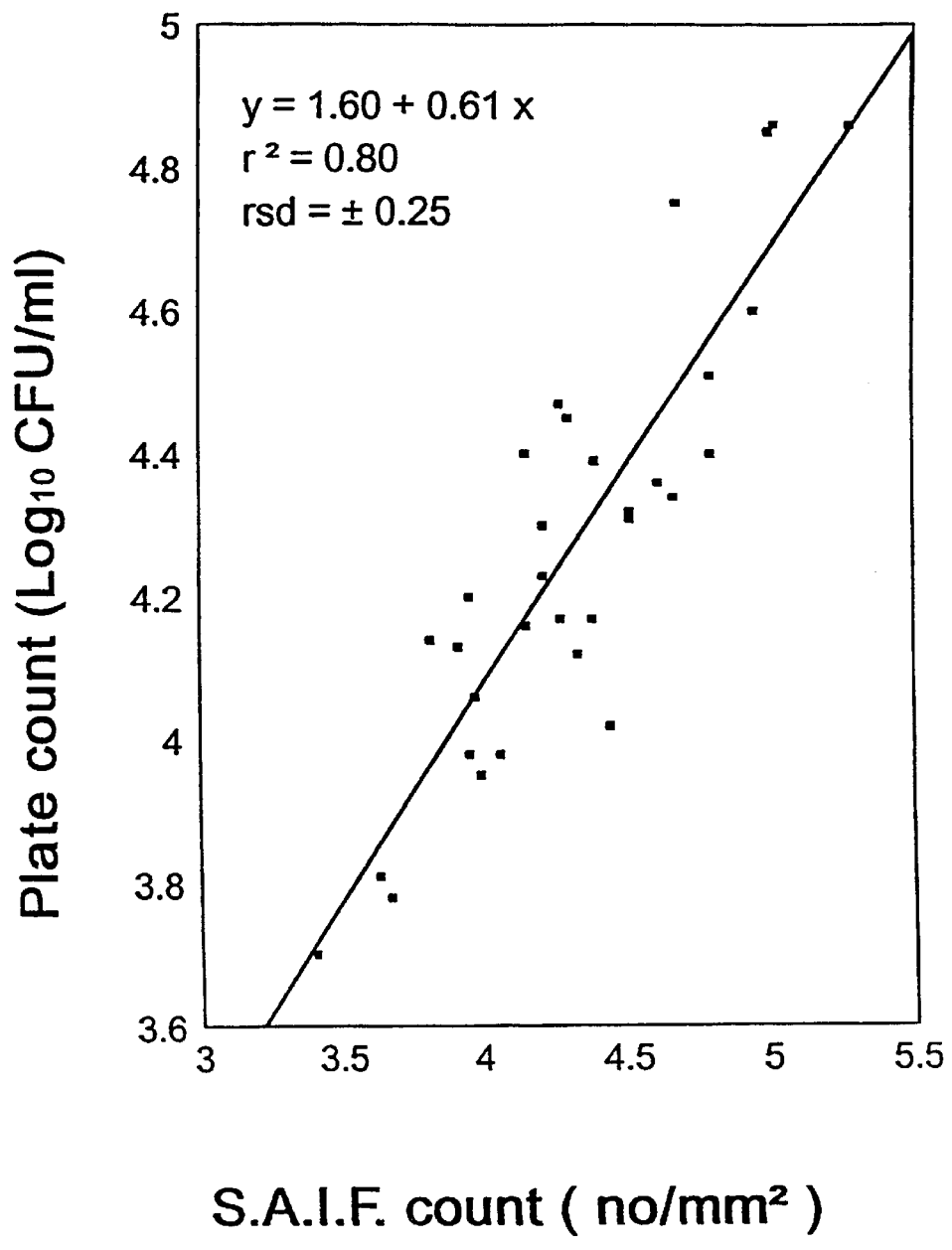

The regression equation generated to predict the standard Listeria count from the S.A.I.F. count was validated using the data from commercial beef mince samples. The experimental S.A.I.F. counts were substituted into the original regression equation to predict the Listeria plate count. The predicted Listeria plate count values were then regressed on the S.A.I.F. values (FIG. 2). The rsd value obtained for the validated samples (±0.25) was similar to that obtained for the original samples (±0.21).

The surface adhesion technique was thus successfully used to isolate bacteria from an enriched meat system.

Optimum attachment of *L. monocytogenes* to the membrane occurred after 15 minutes immersion in the meat culture system. Other workers have also reported that *L. monocytogenes* attached to stainless steel, glass, polypropylene and rubber surfaces within 15–20 min contact time and that longer contact times did not increase the number of Listeria attaching (Mafu et al., 1990; Dickson and Daniels, 1991). However, Fletcher (1977) reported that a contact time as long as 2.5 to 3 h was required for polystyrene to approach saturation with a marine pseudomonad. This difference may be related to differences in adhesive properties between bacterial species and also to the different contact surfaces investigated.

The attachment of *L. monocytogenes* to the membrane did not appear to be affected by the competition from the meat micro-flora. Attachment appeared to be related to numbers rather than types of bacteria in the culture. As the number of Listeria in the culture increased, the number of Listeria attaching to the membrane also increased. Similarly, as the level of the meat microflora in the culture reached a maximum population density the numbers attaching to the membrane also remained constant.

The surface-adhesion immunofluorescent technique had a sensitivity of $\geq \log_{10} 3.01$. The detection level determines the length of sample incubation which is required.

From studies on the growth kinetics of Listeria in meat systems it has been determined that for a sample with a very low initial inocula (1/25 g) an incubation period of 16–18 h incubation would allow the number of Listeria to reach a level of approximately $\log_{10}3.00$/ml (Duffy et al., 1994). Most retail samples, however contain Listeria at levels of around 10–100 CFU/g (Sheridan et al., 1994) and a shorter incubation of 10–12 hours would allow the Listeria in these samples to reach the S.A.I.F. detectable level.

This detection level is very high in relation to a membrane filtration immunofluorescent technique which had a sensitivity of $\log_{10}4.95$–$5.26$/ml (Sheridan et al., 1991) and ELISA techniques which have a detection level of $\log_{10}5$–$6$ cfu/ml. For rapid methods which have a lower sensitivity such as ELISA and PCR a longer incubation period of 48 h is recommended (Walker et al., 1990; Rossen et al., 1991). A slower test means the samples must be stored for longer periods before positive clearance results are obtained.

It was established that once the Listeria numbers in the culture reached a level detectable by the S.A.I.F. method ($\log_{10}3.0$ cfu/ml), there was a linear relationship ($r^2=0.88$) between the number of Listeria in the culture and the S.A.I.F. count (RSD=+0.21). The regression equation generated could be used to accurately predict Listeria plate counts from S.A.I.F. counts. When the S.A.I.F. technique, was applied to commercial beef mince, all samples containing either *L. monocytogenes, L. innocua* or both gave positive results after 14 hours pre-incubation in an enrichment broth. This level of agreement with the standard detection compares well with other rapid methods. A study carried out by Walker et al., (1990) compared the Listeria Tek ELISA kit with cultural procedures for the detection of Listeria from roast chicken (n=26). One false negative and one false positive result was recorded using the ELISA system. Investigations on the use of the Polymerase Chain Reaction to detect *Listeria monocytogenes* from food samples showed perfect agreement with the standard detection methods (Rossen et al., 1991).

The surface adhesion technique would appear to be an ideal presumptive negative test for *L. monocytogenes*. The standard isolation procedure could be continued to determine whether *L. monocytogenes* or *L. innocua* was present. A more specific antibody for *L. monocytogenes* than that used in the present test would give a presumptive positive/negative test for the pathogen.

EXAMPLE 2

The detection of *Yersinia enterocolitica* 0:3 from meat

The use of a surface adhesion technique to isolate *Y. enterocolitica* from an enriched meat system was investigated. Minced beef samples (25 g) inoculated with *Y. enterocolitica* serotype 0:3 (10000 cfu $g^{-1}$) were incubated at 25° C. in Buffered Peptone water for 9 hours.

*Y. enterocolitica* cells were isolated from the enriched meat system by a surface adhesion method. A polycarbonate membrane was attached to a glass microscope slide and immersed in the enriched meat system for 15 minutes. The membrane was washed with a mixture of PBS and tween 80 (0.1%) and coated with anti-*Y. enterocolitica*:0.3 monoclonal antibodies raised in mice and fluorescein isothiocyanate labelled anti-mouse antibody. A Nikon Optiphot microscope with an epifluorescent attachment, a 100 Watt mercury vapour light source and a 60× oil immersion plan objective was used to examine the membrane for the presence of bright green fluorescing *Y. enterocolitica* cells. The total number of fluorescing cells were counted in 20 different fields of vision. The number of cells counted were multiplied by a working factor of 318 (Sheridan et al, 1995).

The technique had a detection level of approximately $\log_{10}3.00$ fu $ml^{-1}$ which is similar to that reported above for the surface adhesion based detection of Listeria. There was good agreement between Yersinia plate counts and the surface adhesion immunofluorescent counts.

EXAMPLE 3

The effect of pH on the surface adhesion of bacteria to membranes

It has been widely reported in the literature that pH has a significant effect on the adhesion of bacteria to surfaces (Kroll, 1985, Thomas, 1988, Litopoulou-Tzanetaki et al, 1989). In general gram positive bacteria adhere better at acidic pH values (4–5) (Wood, 1980) while gram negative adhere bacteria at alkaline pH values (8–9) (Wood, 1980).

A study was conducted to determine the effect of pH on the adhesion of *L. monocytogenes* to membranes. A meat sample (111.0 g) was inoculated with *L. monocytogenes* (10.0 cfu $g^{-1}$) and incubated overnight in buffered peptone water (1000 ml) at 30° C. Following incubation, the test sample was divided and poured into seven separate staining troughs. The pH values of six of the samples were adjusted to 6.40, 4.76, or 3.13 using either an organic (citric) or an inorganic acid (hydrochloric). The pH of the remaining sample was not adjusted and it was used as a control. Each of the seven test solutions was examined for the presence of *L. monocytogenes* using a surface adhesion based technique. A polycarbonate membrane attached to a glass microscope slide was immersed in the test solution for 15 min. The membrane was washed with PBS and Tween 80 (0.1%) and coated with anti *L. monocytogenes* monoclonal antibody and FITC labelled antibody. The membrane was examined under UV light and green fluorescing Listeria cells were counted in 20 fields and multiplied by a working factor of 318 to obtain the number of Listeria per $mm^2$ of membrane.

The results showed that at low pH values (3.13–4.76) the adhesion of Listeria to the membranes was significantly increased, thus rendering the technique more sensitive. The choice of an organic or an inorganic acid to lower the pH of the test solution did not affect the adhesion of Listeria.

The S.A.I.F. assay is simple to carry out taking approximately 15 min to carry out the separation stage and one hour to carry out the immunofluorescent detection procedure. The amount of labour is minimal and all materials are those used routinely in standard detection methods. The only capital expenditure is the fluorescent microscope while the day to day to running cost of this test is minimal. It would also appear to be robust enough for routine use in a laboratory in industry.

The S.A.I.F. technique used manual counting of the Listeria cells using fluorescence microscopy. Automating the counting procedure would, however, be possible. An image analysis system similar to used in the AODC technique for total bacterial counts may be employed (Duffy et al., 1991). Alternatively a detection system based on a ELISA colour reaction may be used.

The polycarbonate membrane surface used in the above Examples is an inanimate surface and attachment appears to be non-specific though possibly related to bacterial species concentrations. However, the use of biological surfaces for attachment offers the possibility for more selective attachment. A surface such as a turkey skin or sausage casing could be employed, in the same manner as the membrane was used in the present investigation to isolate Listeria or other pathogens from an enriched food system. The skin/casing could be cut in suitable size discs, attached to a solid support and immersed in the test solution. A particular bacterial species attached to the skin/casing could be detected by immunofluorescence.

TABLE 1

RELATIONSHIP BETWEEN IMMERSION TIME AND THE NUMBER OF LISTERIA AND MEAT MICROORGANISMS ADHERING TO A MEMBRANE IMMERSED IN A MEAT CULTURE PREPARED FROM BUFFERED PEPTONE WATER

| IMMERSION TIME (MIN) | MEAN LISTERIA COUNT ($LOG_{10}$ CFU/ML) | MEAN TVC COUNT ($LOG_{10}$ CFU/ML) |
|---|---|---|
| 5 | 2.87 | 10.25 |
| 10 | 3.00 | 10.55 |
| 15 | 3.25 | 10.75 |
| 20 | 3.23 | 10.40 |
| 30 | 3.24 | 10.41 |
| 40 | 3.21 | 10.46 |
| 50 | 3.23 | 10.42 |
| 60 | 3.18 | 10.42 |

TABLE 2

ESTIMATION OF BACTERIAL NUMBERS ADHERING TO A MEMBRANE BY STANDARD PLATE METHOD AND A SURFACE ADHESION IMMUNOFLUORESCENT TECHNIQUE

| TIME (H) | LISTERIA ($LOG_{10}$ CFU/ML) | TVC ($LOG_{10}$ CFU/ML) | NUMBER OF LISTERIA ON MEMBRANE ($LOG_{10}$ CFU) | TVC ON MEMBRANE ($LOG_{10}$) | IMMUNO-FLUORESCENT COUNT (NO. CELLS IN 20 FIELDS) |
|---|---|---|---|---|---|
| 8 | 2.69 | 12.82 | 2.10 | 8.61 | 0 |
| 10 | 3.01 | 12.95 | 2.68 | 8.72 | 2 |
| 12 | 4.04 | 12.98 | 3.51 | 8.95 | 15 |
| 14 | 5.02 | 13.54 | 3.97 | 9.61 | 47 |
| 16 | 5.47 | 13.97 | 4.67 | 9.40 | 119 |
| 18 | 6.08 | 13.99 | 4.93 | 9.54 | 159 |
| 20 | 6.67 | 13.98 | 5.58 | 9.53 | 217 |

TABLE 3

A COMPARISON OF A STANDARD METHOD AND A RAPID METHOD FOR THE DETECTION OF LISTERIA SPP. FROM COMMERCIAL BEEF MINCE SAMPLES

| LISTERIA SPP. DETECTED BY STANDARD METHOD | NUMBER OF POSITIVE SAMPLES (STANDARD METHOD) | NUMBER OF POSITIVE SAMPLES (RAPID METHOD) |
|---|---|---|
| L. monocytogenes | 8 | 8 |
| L. innocua | 12 | 12 |
| L. monocytogenes/ L. innocua | 10 | 10 |
| L. innocua/ L. welshimeri | 2 | 2 |
| L. innocua/ L. monocytogenes/ L. welshimeri | 1 | 1 |
| L. welshimeri | 2 | 0 |
| negative | 15 | 15 |
| Total | 50 | 48 |

REFERENCES

Absolom, D. R., Lamberti, F. V., Policova, Z., Zingg, W., van Oss, C. J., Neuman, W. (1983) Surface thermodynamics of bacterial adhesion. Appl. Environ. Microbiol. 46: 1, 90–97.

Brown, M. R. W., Williams, P. (1985) The influence of environment on envelope properties affecting survival of bacteria in infections. Ann. Rev. Microbiol. 39: 527–556.

Chung, K. T., Dickson, J. S., Crouse, J. D., (1989). Attachment and proliferation of bacteria on meat. J. Food Prot. 52: 173–177.

Dazzo, F. B., (1980). Microbial adhesion to plant surfaces. Microbial adhesion to surfaces. Ellis Horwood Ltd. Publishers. 311–324.

Dickson, J. S., Daniels, K. E. (1991) Attachment of S. typhimurium and L. monocytogenes to glass as affected by surface film thickness, cell density and bacterial motility. J. Ind. Microbiol.8: 281–284.

Donnelly, C. W., Baigent, G. J., (1986). Method for flow cytometric detection of Listeria monocytogenes in milk. Appl. Env. Microbiol. 52: 4, 689 695.

Duffy, G. Sheridan, J. J., McDowell, D. A., Blair, I. S., Harrington, D. (1991). The use of Alcalase 2.5 L in the Acridine orange direct count technique for the enumeration of bacteria in beef mince Letters Appl. Microbiol. 13: 198–201.

Duffy, G. Sheridan, J. J., Buchanan, R. L., McDowell, D. A., Blair, I. S. (1994). The effect of aeration, initial inoculum and meat microflora on the growth kinetics of L. monocytogenes in selective broths. Food Microbiol. 11: 429–438.

Farber, J. M., Idziak, E. S, (1984). Attachment of psychrotrophic meat spoilage bacteria to muscle surfaces. J. Food Prot. 47: 2, 92–95.

Firstenberg-Eden, R., Notermans, S., Van Schothorst, M. (1978). Attachment of certain bacterial strains to chicken and beef meat. J. Food safety 1: 217–218.

Firstenberg-Eden, R., (1981). Attachment of bacteria to meat surfaces: A review. J. Food Prot. 8: 602–607.

Fletcher, M. (1977). The effects of culture concentration and age, time, and temperature on bacterial attachment to polystyrene. Can. J. Microbiol. 23: 1–6.

Fletcher, M., Floodgate, G. D. (1973). An electron—microscopic demonstration of an acidic polysaccharide involved in the adhesion of marine bacterium to solid surfaces. J. General. Microbiol. 74: 325–334.

Fletcher, M., Loeb, G. L. (1979). Influence of substratum characteristics on the attachment of a marine pseudomonad to solid surfaces. Appl. Environ. Microbiol. 37: 1, 67–72.

Gelinas, P., Goulet J., (1983). Efficacite de huit desinfectants sur trois types de surfaces contaminees par Ps. aeruoinosa. Can. J. Microbiol. 24: 1715–1730.

Herald, P. J., Zottola, E. A., (1988) Attachment of L. monocytogenes to stainless steel surfaces at various temperatures and pH values. J. Food Sci. 53: 5, 1549–1552.

Jeong Weon, K., Knabel, S. J., Doores, Stephanie, (1993). Penetration of Salmonella typhimurium into turkey skin. J. Food Prot. 56: 292–296.

Kroll, R. G. (1980). Electropositively charged filters for the concentration of bacteria from foods. Food Microbiol. 2, 183–186.

Litopoulou-Tzanetaki, E., Bayliss, A., Patchett, R. A. and Kroll, R. G. (1989) Adsorption of bacteria to ion-exchange materials. Lett. Appl. Micro. 9, 219–222.

Mafu, A. A., (1990) Attachment of L. monocytogenes to stainless steel, glass, polypropylene and rubber surfaces after short contact times. J. Food Prot. 53: 9, 742–746.

McClain, D. and Lee, W. H. (1987) Isolation and identification of *L. monocytogenes* from meat. USDA-FSIS Microbiol. Div., Laboratory Communication No. 57.

Rossen, L., Holmstrom, Olsen, J. E., Rasmussen, O. F. (1991). A rapid polymerase chain reaction (PCR) based assay for the identification of *Listeria monocytogenes* in food samples. *Int. J. Fd. Microbiol.* 14: 145–152.

Selgas, Dolores, Marin, M. Luisa, Pin, Carmen, Casas, Carmen (1993). Attachment of bacteria to meat surfaces: A review. *Meat Sci.* 34: 265–273.

Sheridan, J. J., Walls, I., McDowell, D. A., Welch, R. (1991). Use of a microcolony technique combined with an indirect immunofluorescence test for the rapid detection of Listeria in raw meat. *Letters Appl. Microbiol.* 13: 140–144.

Sheridan, J. J., Duffy, G., McDowell, D. A., Blair, I. S. (1994). The occurrence and initial numbers of Listeria in Irish meat and fish products and the recovery of injured cells from frozen products. *Int. J. Food Microbiol.* 22: 105–113.

Sheridan, J. J., Duffy, G., McLauchlin, J., McDowell, D. A., Blair, I. S. (1995). Use of a surface adhesion immunofluorescent technique for the rapid detection of Listeria from meat. In press.

Thomas, Susan, D. (1988). Electropositively charged filters for the recovery of yeasts and bacteria from beverages. *J. Appl. Bacteriol.* 65, 35–41.

Van Loosdrecht, M. C. M., Lyklema, J., Norde, W., Schraa, G., Zehnder, A. J. B, (1987). The role of bacterial cell wall hydrophobicity in adhesion. *Appl. Environ. Microbiol.* 53: 1893–1897.

Walker, P. D., Nagy, L. K., (1980). Adhesion of organisms to animal tissues. Microbial adhesion to surfaces. Ellis Horwood Ltd. Publishers 473–493.

Walker, S. J., Archer, P., Appleyard, J. (1990). Comparison of the Listeria-tek ELISA kit with cultural procedures for the detection of Listeria sps. in foods. *Food Microbiol.* 7: 335–342.

Walls, Isabel, Sheridan J. J., Welch, R. W., McDowell, D. A., (1989). A rapid method of enumerating microorganisms from beef, using an Acridine Orange Direct Count technique. *Ir. J. Fd. Sci. Technol.* 13: 23–31.

Walls, Isabel, Cooke, P. H., Benedict, R. C., Buchanan, R. L. (1993). Factors affecting attachment of *Salmonella typhimurium* to sausage casings. *Food Microbiol.* 10: 387–393.

Wood, J. M. (1980) The interaction of microorganisms with ion-exchange resins. In *Microbiol Adhesion to Surfaces* ed. Berkeley, R. C. W., Lynch, J. M., Melling, J., Rutter, P. R. and Vincent, B. pp 163–185. Chichester: Ellis Horwood.

What is claimed is:

1. A method for the rapid detection of bacteria in a liquid culture suspected to contain bacteria, comprising the steps of
immersing a membrane mounted on a solid support in a liquid culture for a time sufficient to allow bacteria to adhere to the membrane by surface adhesion;
removing the membrane from the liquid culture; and
counting the number of bacteria adhering to the membrane.

2. The method according to claim 1 wherein the membrane is an inanimate membrane.

3. The method according to claim 1 wherein the membrane is a biological membrane.

4. The method as claimed in claim 1 wherein the solid support is selected from a glass microscope slide, a plastics slide, or a wire frame.

5. The method as claimed in claim 1 wherein the membrane is immersed in the liquid culture for at least 10 minutes at between 25 and 30° C. and at a pH of about 4.0.

6. The method as claimed in claim 1 wherein the membrane is coated with a labelled anti-bacterial antibody following removal of the membrane from the liquid culture.

7. The method as claimed in claim 6 wherein the antibody is a monoclonal antibody.

8. The method as claimed in claim 7 wherein the antibody is an anti-Listeria antibody, or an anti-Yersinia antibody.

9. The method as claimed in claim 6 wherein the membrane is washed between removal from the liquid culture and coating with the antibody.

10. The method as claimed in claim 6 wherein the labeled antibody is labeled with fluorescein isothiocyanate, tetramethylrhodamine, horseradish peroxidase, alkaline phosphatase, or glucose oxidase.

11. The method as claimed in claim 10 wherein a fluorescent label is used, the membrane is examined under an ultra-violet light microscope and a count of fluorescing labeled cells is made.

12. The method as claimed in claim 10 wherein a laser scanning system is used to scan the membrane and count labelled cells.

13. The method according to claim 1 wherein the liquid culture is prepared by immersion of a solid or semi-solid food substance in a liquid.

14. The method as claimed in claim 13 wherein the solid or semi-solid substance is macerated before immersion in the liquid.

15. The test kit for the rapid detection of bacteria in a liquid culture suspected to contain bacteria by surface adhesion, comprising a membrane mounted on a solid support and a labelled anti-bacterial antibody.

16. The kit as claimed in claim 15 further comprising a substrate.

17. The kit as claimed in claim 15 further comprising an enzyme-labelled conjugate or a fluorescent-labelled conjugate.

18. A kit as claimed in claim 15 wherein the membrane is selected from an inanimate membrane, a membrane based on a cellulose derivative, a polyamide membrane, a nylon membrane, an inorganic membrane, an ion exchange membrane and a biological membrane.

19. The method of claim 5, wherein the pH is in the range 3.13 to 4.76.

20. A kit according to claim 18 wherein said inanimate membrane is selected from the group consisting of:
a polycarbonate membrane;
a polyvinyl chloride membrane;
an acetate, nitrate, or ester derivative of cellulose;
a polyamide membrane;
a nylon membrane;
an ion exchanging membrane; and
an inorganic membrane including silver or aluminium.

21. The kit according to claim 15 wherein the membrane is a biological membrane.

22. The kit according to claim 21 wherein said biological membrane is selected from the group consisting of:
an animal skin; a collagen membrane; and an animal internal membrane.

23. The kit according to claim 22 wherein said biological membrane is an animal internal membrane or sausage casing.

24. A method according to claim 2 wherein said inanimate membrane is selected from the group consisting of:

a polycarbonate membrane;
a polyvinyl chloride membrane;
an acetate, nitrate, or ester derivative of cellulose;
a polyamide membrane;
a nylon membrane;
an ion exchanging membrane; and
an inorganic membrane including silver or aluminium.

25. The method according to claim 3 wherein said biological membrane is selected from the group consisting of: an animal skin; a collagen membrane; and an animal internal membrane.

* * * * *